United States Patent [19]

Banks et al.

[11] Patent Number: 4,966,923
[45] Date of Patent: Oct. 30, 1990

[54] POLYMERIZABLE COMPOSITIONS

[75] Inventors: Christopher P. Banks, Saffron Walden; Edward Irving, Burwell, both of England; Alfred Renner, Muntelier, Switzerland; Terence J. Smith, Royston, England

[73] Assignee: Ciba-Geigy Corporation, Ardsley, N.Y.

[21] Appl. No.: 120,044

[22] Filed: Nov. 13, 1987

[30] Foreign Application Priority Data

Nov. 22, 1986 [GB] United Kingdom ............... 8628003

[51] Int. Cl.$^5$ ................................................ C08F 2/46
[52] U.S. Cl. ................................. 522/167; 526/259; 526/262
[58] Field of Search ............... 526/259, 262; 522/167

[56] References Cited

U.S. PATENT DOCUMENTS

| | | |
|---|---|---|
| 4,045,223 | 8/1977 | Rubner et al. ............... 96/35.1 |
| 4,115,368 | 9/1978 | Roth et al. ............... 526/262 X |
| 4,515,962 | 5/1985 | Renner ............... 548/435 |
| 4,579,916 | 4/1986 | Schmid et al. ............... 525/502 |
| 4,587,317 | 5/1986 | Renner ............... 526/259 |
| 4,604,437 | 8/1986 | Renner ............... 526/260 |
| 4,666,997 | 5/1987 | Renner et al. ............... 525/502 |
| 4,709,047 | 11/1987 | Renner et al. ............... 548/435 |

FOREIGN PATENT DOCUMENTS 152371 8/1985 European Pat. Off. .
166693 1/1986 European Pat. Off. .

Primary Examiner—Joseph L. Schofer
Assistant Examiner—J. M. Reddick
Attorney, Agent, or Firm—Luther A. R. Hall

[57] ABSTRACT

A polymerizable composition comprises a mixture of
(A) a substance having at least one allyl- or methallyl-substituted bicyclo[2.2.1]-hept-5-ene-2,3-dicarboxylic acid imide residue, and
(B) a substance having at least one polymerizable residue of formula $$CH_2=C(R^1)COO- \qquad I$$

where $R^1$ denotes a hydrogen atom or a methyl group.

Typically, (A) is bis[4-(allylbicyclo[2.2.1]hept-5-ene-2,3-dicarboximidophenyl)]methane and (B) is an acrylate or methacrylate of a polyhydric alcohol. The compositions can be photopolymerized or heat-cured. They are suitable for use in prepreg manufacture and in image formation.

12 Claims, No Drawings

POLYMERIZABLE COMPOSITIONS

This invention relates to polymerisable compositions containing a mixture of a substituted bicyclo[2.2.1]hept-5-ene-2,3-dicarboxylic acid imide and a polymerisable acrylic material, their polymerisation and their uses.

Allyl- or methallyl-substituted bicyclo[2.2.1]hept-5-ene-2,3-dicarboxylic acid imides and their use for the preparation of polymers by heating to 180°–300° C. are described in European Patent Publication Nos. 0 105 024 and 0 152 372. The formation of crosslinked polymers by heating imides of this type in the presence of a cationic polymerisation catalyst is described in European Patent Publication No. 0 155 435.

Heat-curable compositions containing an epoxide resin, an imide of the type disclosed in European Patent Publication No. 0 105 024 and a curing agent for the resin are described in European Patent Publication No. 0 146 498. The latter suggests that the curable compositions can contain flow control agents, including liquid acrylic resins. The liquid acrylic resins conventionally used as flow control agents in epoxide resin compositions are polymerised acrylic materials containing no polymerisable acrylic unsaturation.

It has now been found that compositions containing an allyl- or methallyl-substituted bicyclo[2.2.1]hept-5-ene-2,3-dicarboxylic acid imide and a polymerisable acrylic material can be photopolymerised to give polymeric materials useful in the production of fibre-reinforced composites or in image formation and can be thermally cured to give products having excellent physical properties.

Accordingly, the present invention provides a polymerisable composition comprising a mixture of (A) a substance having at least one allyl- or methallyl-substituted bicyclo[2.2.1]-hept-5-ene-2,3-dicarboxylic acid imide residue, and (B) a substance having at least one polymerisable residue of formula

$$CH_2=C(R^1)COO— \qquad I$$

where $R^1$ denotes a hydrogen atom or a methyl group.

The imide residue in (A) is usually unsubstituted, other than by allyl or methallyl, in the bicycloheptene ring or is further substituted by an alkyl group. Preferred imide residues are those of formula

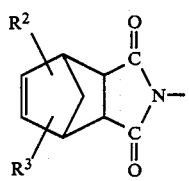

II where
$R^2$ denotes allyl or methallyl and
$R^3$ denotes a hydrogen atom or methyl group.

The composition preferably contains a mixture of at least one imide having one, two or three groups of formula II and at least one acrylic material having at least one group of formula I, particularly at least 2, more particularly 2 to 4, groups of formula I. In this embodiment, preferred imides are those of formula

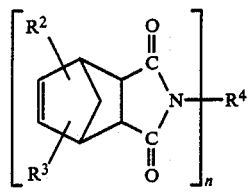

III where
n denotes 1, 2 or 3,
$R^2$ denotes allyl or methallyl,
$R^3$ denotes a hydrogen atom or methyl group, and
$R^4$, when n is 1, denotes a hydrogen atom, a hydroxyl group, or a monovalent organic residue having preferably 1 to 40 C-atoms, or
$R^4$, when n is 2, denotes a divalent organic residue, having preferably 2 to 20 C-atoms, or
$R^4$, when n is 3, denotes a trivalent organic residue having preferably 6 to 126 C-atoms.

In formula III, $R^2$ preferably denotes allyl and $R^3$ denotes a hydrogen atom.

When n is 1, $R^4$ may denote an aliphatic, cycloaliphatic, aromatic or araliphatic organic group. Preferably $R^4$ denotes a hydrogen atom, a hydroxyl group, or an organic group selected from $C_1$–$C_{40}$ alkyl, optionally interrupted in the chain by oxygen atoms, $C_3$–$C_6$ alkenyl, $C_5$–$C_{20}$ cycloalkyl, $C_6$–$C_{20}$ aryl or benzyl, any of these organic groups optionally being substituted by a hydroxyl group, or a group of formula

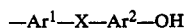

$$—Ar^1—X—Ar^2—OH \qquad IV$$

where
$Ar^1$ and $Ar^2$ each denote a phenylene group and X denotes methylene, isopropylidene, —CO—, —O—, —S— or —SO$_2$—.

When n is 2, $R^4$ may denote an aliphatic, cycloaliphatic, aromatic or araliphatic group. Preferably $R^4$ denotes $C_2$ to $C_{20}$ alkylene, optionally interrupted in the chain by oxygen atoms or secondary amino groups, $C_6$ to $C_{20}$ arylene or a group of formula

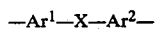

$$—Ar^1—X—Ar^2— \qquad V$$

where $Ar^1$, $Ar^2$ and X are as defined in formula IV.

When n is 3, $R^4$ may denote an aliphatic or aromatic group. Preferably $R^4$ denotes a group of formula

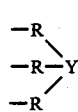

VI where
Y denotes >P=O or >P— and R denotes an alkylene group of 2 to 40 carbon atoms, optionally interrupted in the chain by oxygen atoms, a m- or p-phenylene group, or a m- or p-phenyleneoxy group in which the oxygen atom is bonded to the group Y, or Y denotes >CH— and R denotes a m- or p-phenylene group, or Y denotes $CH_3CH_2C(CH_2)_3$ or —$CH_2CHCH_2$— and R denotes an oxyalkylene group of 2 or 3 carbon atoms, a polyoxyethylene or polyoxypropylene group of 4 to 40 carbon atoms, or a m- or p-phenyleneoxy group in which the oxygen atom is attached to the group Y, or Y denotes >N— and R denotes an alkylene group of 2 to 10 carbon atoms, or a m- or p-phenylene group.

Where $R^4$ denotes an optionally interrupted $C_1$–$C_{40}$ alkyl group, it may be a straight or branched chain alkyl group such as methyl, ethyl, isopropyl, n-butyl, isopentyl, n-hexyl, 2-ethylhexyl, n-decyl and n-dodecyl, but is preferably $C_1$–$C_8$ alkyl. When $R^4$ denotes $C_3$–$C_6$ alkenyl, it may also have a straight or branched chain and may be, for example, allyl, methallyl, 2-butenyl or 3-hexenyl, with allyl being preferred. A cycloalkyl group $R^4$ may be a cyclopentyl, cyclohexyl, cycloheptyl or cyclooctyl group, with cyclohexyl being preferred.

An aryl group $R^4$ may be phenyl, phenyl substituted by one or two methyl groups, e.g. tolyl or xylyl, or naphthyl, with phenyl being preferred.

When $R^4$ denotes a hydroxy substituted alkyl group, it may be a $C_1$ to $C_{40}$ hydroxyalkyl group such as methylol, 2-hydroxyethyl, 2-hydroxypropyl, 3-hydroxypropyl, 4-hydroxybutyl, 5-hydroxypentyl, 2,2-dimethyl-3-hydroxypropyl, 8-hydroxyoctyl, 12-hydroxydodecyl, 16-hydroxyhexadecyl or 2,3-dihydroxypropyl; or a $C_2$ to $C_{40}$ hydroxyalkyl group interrupted in the chain by oxygen atoms, such as 2-hydroxyethoxyethyl, 3-hydroxypropoxypropyl and other hydroxyalkoxyalkyl groups of formula —$CH_2CH_2(OCH_2CH_2)_p$— where p denotes 1 to 15 or —$CH_2CH_2CH_2(OCH_2CH_2CH_2)_q$— where q denotes 1 to 10. Preferred hydroxyalkyl groups $R^4$ are $C_2$ to $C_8$ alkyl groups substituted by 1 or 2 hydroxyl groups and optionally interrupted in the chain by 1 to 3 oxygen atoms.

When $R^4$ denotes a hydroxy substituted cycloalkyl group, it may be a mononuclear or polynuclear group such as hydroxycyclopentyl, hydroxycyclohexyl, hydroxycyclooctyl, hydroxycyclohexylcyclohexylmethane and 2-hydroxycyclohexyl-2-cyclohexylpropane, but is preferably a $C_5$ to $C_8$ mononuclear group, particularly hydroxycyclohexyl. A hydroxyaryl group $R^4$ may be m- or p-hydroxyphenyl or hydroxynaphthyl, any of which may be substituted by one or more $C_1$–$C_4$ alkyl groups, such as methyl, ethyl or propyl. Preferred hydroxyaryl groups are m- and p-hydroxyphenyl, the latter being particularly preferred.

Preferred groups $R^4$ of formula IV are those where X denotes methylene, isopropylidene, —O—, or —$SO_2$—.

When n is 2, suitable alkylene groups $R^4$ are straight or branched chain groups such as ethylene, 1,2-propylene, trimethylene, tetramethylene, hexamethylene, octamethylene and dodecamethylene, and alkylene groups interrupted in the chain by one or more oxygen atoms or secondary amino groups, such as polyoxyethylene, polyoxypropylene and polyiminoethylene groups. Preferred alkylene groups $R^4$ are $C_2$ to $C_{12}$ straight chain alkylene groups.

An arylene group $R^4$ may be m-phenylene, p-phenylene, 1,3-naphthylene, 1,4-naphthylene, 1,5-naphthylene or 2,6-naphthylene, with m- and p-phenylene groups being preferred.

When $R^4$ denotes a group of formula V, it is preferably a group where X denotes methylene, —O— or —$SO_2$—, the indicated free valencies in formula V preferably being in the 4 and 4' positions.

When n is 3, suitable groups of formula VI include those where Y denotes →P=O or >P— and R denotes ethylene, 1,2- or 1,3-propylene, tetramethylene, hexamethylene, decamethylene, hexadecamethylene, ethyleneoxy, 1,2- or 1,3-propyleneoxy, n-butyleneoxy or n-hexyleneoxy, with groups where R denotes an alkylene group of 2 to 4 carbon atoms, a m- or p-phenylene or a m- or p-phenyleneoxy group being preferred.

Where Y denotes >CH—, R preferably denotes a p-phenylene group.

Suitable groups of formula VI where Y denotes $CH_3CH_2C(CH_2)_3$ include those where R denotes ethyleneoxy, 1,2- or 1,3-propyleneoxy, a polyoxyethylene group of 4 to 20 carbon atoms or a polyoxypropylene group of 6 to 30 carbon atoms, with groups where R denotes a group —[$CH_2CH(CH_3)O$]$_r$—, where r is 1, 2 or 3, being preferred.

Suitable groups of formula VI where Y denotes —$CH_2CHCH_2$— include those where R denotes ethyleneoxy, 1,2- or 1,3-propyleneoxy, a polyoxyethylene group of 4 to 20 carbon atoms or a polyoxypropylene group of 6 to 30 carbon atoms, with groups where R denotes a group —($CH_2CH_2O$)$_r$—, where r is 1, 2 or 3, or a m- or p-phenyleneoxy group being preferred.

Suitable groups of formula VI where Y denotes >N— include those where R denotes ethylene, 1,2- or 1,3-propylene, 1,4-butylene or 1,6-hexylene, with groups where R denotes ethylene, trimethylene or m- or p-phenylene being preferred.

Preferred compositions contain imides of formula III where n is 1 and $R^4$ denotes a hydrogen atom, a hydroxyl group, $C_1$–$C_8$ alkyl, allyl, cyclohexyl, phenyl, benzyl, $C_2$–$C_8$ alkyl substituted by one or two hydroxyl groups and optionally interrupted in the chain by one to three oxygen atoms, hydroxycyclohexyl, hydroxyphenyl, or a group of formula IV where X denotes methylene, isopropylidene, —O— or —$SO_2$—, those where n is 2 and $R^4$ denotes $C_2$–$C_{12}$ straight chain alkylene, m- or p-phenylene or a group of formula V where X denotes methylene, —O— or —$SO_2$—, and those where n is 3 and $R^4$ denotes a group of formula VI where Y denotes >P=O or >P— and R denotes an alkylene group of 2 to 4 carbon atoms, a m- or p-phenylene group or a m- or p-phenyleneoxy group, or Y denotes >CH— and R denotes a p-phenylene group, or Y denotes $CH_3CH_2C(CH_2)_3$ and R denotes a group —[$CH_2CH(CH_3)O$]$_r$— where r is 1, 2 or 3, or Y denotes —$CH_2CHCH_2$— and R denotes a group —($CH_2CH_2O$)$_r$ where r is 1, 2 or 3, or a m- or p-phenyleneoxy group, or Y denotes >N— and R denotes an ethylene, trimethylene, or m- or p-phenylene group.

Particularly preferred compositions contain imides of formula III in which $R^2$ denotes allyl, $R^3$ denotes a hydrogen atom, and n is 1 and $R^4$ denotes a hydroxyl group, allyl, 2-hydroxyethyl or p-hydroxyphenyl or n is 2 and $R^4$ denotes —($CH_2$)$_6$—,

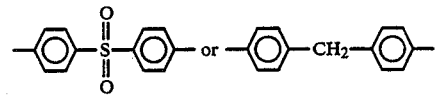

or n is 3 and $R^4$ denotes

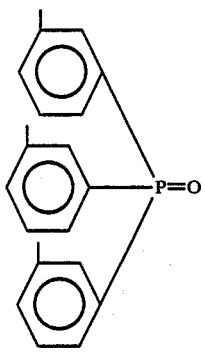

Mixtures of two or more of the above imides can be used.

In particularly preferred compositions of the invention there are used as the imide component bis(4-(allyl-bicyclo[2.2.1]hept-5-ene-2,3-dicarboximidophenyl))methane, a mixture thereof with N-allyl-allylbicyclo[2.2.1-]hept-5-ene-2,3-dicarboximide and N,N'-hexamethylene-bis(allylbicyclo[2.2.1]hept-5-ene-2,3-dicarboximide, and a mixture of the last two compounds.

Compounds having an imide residue of formula II can be prepared by known processes, for example by reacting an anhydride of formula

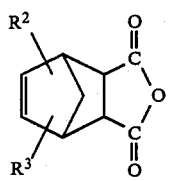
VII where $R^2$ and $R^3$ are as defined for Formula II with a compound having at least one primary amine group at elevated temperature.

Imides of formula III can be prepared, for example, by the process described in EP-A No. 0 105 024, by reacting an anhydride of formula VII with a compound of formula

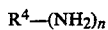
VIII where $R^4$ and n are as defined for formula III, at elevated temperature while distilling off water formed during the reaction. When the compound of formula VIII is ammonia or a low-boiling monoamine, an excess of this reactant is generally used. Amines of formula VIII are conveniently used in stoichiometric proportion. The reaction can be carried out without a solvent or in the presence of an inert solvent suitable for the azeotropic removal of the water (entrainer). The reaction temperature is usually from 100° to 250° C. Alternatively, the reaction can be carried out in the melt in general under pressure of up to 4500 Pa at a temperature from 130° to 220° C., particularly from 180° to 220° C. Imides of formula III where n is 3 and $R^4$ denotes a group of formula IV, where Y denotes >P=O or >P— and R denotes an alkylene-oxy or m- or p-phenyleneoxy group, can also be prepared by reacting an imide of formula III, where n is 1 and $R^4$ denotes a hydroxyalkyl or m- or p-hydroxyphenyl group, with a phosphorus oxyhalide or phosphorus trihalide, preferably phosphorus oxychloride, phosphorus tribromide or phosphorus trichloride, in the presence of a base, usually a tertiary amine, the reaction usually being carried out in an inert organic solvent at 0°-30° C.

Preferred components (B) are acrylic materials having at least two groups of formula I which are esters of a carboxylic acid containing a group of formula I with a polyhydric alcohol or phenol or an epoxide resin.

The carboxylic acid containing a group of formula I may be acrylic acid, methacrylic acid or an adduct formed by reacting a hydroxyalkyl acrylate or hydroxyalkyl methacrylate with a polycarboxylic acid anhydride. Preferred adducts are those derived from 2-hydroxyethyl, 2-hydroxypropyl or 3-hydroxypropyl acrylate or methacrylate and saturated or unsaturated aliphatic anhydrides such as succinic, adipic, glutaric or maleic anhydride, cycloaliphatic anhydrides such as tetrahydrophthalic or hexahydrophthalic anhydride, or aromatic anhydrides such as phthalic, trimellitic or pyromellitic anhydride. Preferred esters are those of acrylic and methacrylic acids, i.e. polyacrylate and polymethacrylate esters of polyhydric alcohols and phenols and epoxide resins.

Polyhydric alcohols from which the esters may be derived include those having from 2 to 10 alcoholic hydroxyl groups. Such alcohols may be aliphatic, cycloaliphatic, heterocyclic or aromatic compounds.

Where the polyhydric alcohol is aliphatic, it may have from 2 to 6 hydroxyl groups and from 2 to 60 carbon atoms. Suitable alcohols include diols such as alkylene glycols, for example ethylene, 1,2-propylene, trimethylene, tetramethylene, neopentylene, hexamethylene, octamethylene and dodecamethylene glycols, oxyalkylene glycols such as di(ethylene glycol) and di(propylene glycol) and adducts of the above alkylene glycols with one mol of ethylene oxide or propylene oxide, and polyoxyalkylene glycols such as polyoxyethylene glycols, for example di-, tri- and tetra-ethylene glycols, and higher polyoxyethylene glycols having up to 40 carbon atoms, polyoxypropylene glycols, for example polyoxypropylene glycols having from 6 to 60 carbon atoms, such as tri-propylene glycol, and adducts of the alkylene glycols mentioned above with more than one mol of ethylene oxide or propylene oxide. Suitable aliphatic triols include glycerol, 1,1,1-trimethylolpropane and their adducts with ethylene oxide or propylene oxide. Where the aliphatic alcohol from which the ester is derived is a tetrol, it may be erythritol, pentaerythritol, or their adducts with ethylene oxide or propylene oxide. When the aliphatic polyhydric alcohol is pentol, it may be arabitol, xylitol or their adducts with ethylene oxide or propylene oxide. Suitable aliphatic hexols include dipentaerythritol, mannitol, sorbitol, and their adducts with ethylene oxide or propylene oxide.

Cycloaliphatic polyhydric alcohols from which the esters may be derived are usually cycloaliphatic compounds having from 2 to 6 hydroxyalkyl substituents, for instance $C_5$ to $C_8$ mononuclear cycloaliphatic compounds having two or three hydroxyalkyl substituents, preferably a di- or tri- hydroxymethyl- or hydroxyethyl-substituted cyclohexane.

Where the polyhydric alcohol from which the ester is derived is a heterocyclic alcohol, it may be a heterocyclic compound having from 2 to 6 hydroxyalkyl substituents, for instance a 5- or 6-membered heterocycle having 2 or 3 hydroxyalkyl substituents, preferably a di- or tri-hydroxymethyl- or hydroxyethyl-substituted 5- or 6-membered heterocycle such as isocyanuric acid, uracil, urazole, or uric acid, especially tris(2-hydroxyethyl)isocyanurate.

Aromatic polyhydric alcohols from which the esters can be derived are usually aromatic compounds having from 2 to 8 hydroxyalkyl substituents, including mononuclear compounds such as di- and tri-methylolphenol, and polynuclear compounds such as phenol-formaldehyde resole resins, and adducts of these mononuclear and polynuclear compounds or polyhydric phenols with ethylene oxide or propylene oxide. Preferred aromatic alcohols are 1,3-dimethylolbenzene, 1,3,5-trimethylolbenzene and, particularly, 2,2-bis(p-(2-hydroxyethoxy)phenyl)propane.

The esters of polyhydric alcohols are mostly known compounds or may be made by well-known processes. They may be prepared by reacting the carboxylic acid having a group of formula I, preferably acrylic or methacrylic acid or, more usually, an esterifying derivative thereof, such as acrylyl or methacrylyl chloride, with the polyhydric alcohol. Where the latter contains more than two hydroxyl groups, two hydroxyl groups may be esterified and one or more of the remaining hydroxyl groups left unesterified.

Polyhydric phenols from which the esters may be derived include mononuclear phenols such as resorcinol, bisphenols such as bis(4-hydroxyphenyl)methane and 2,2-bis(4-hydroxyphenyl)propane and novolaks derived from phenol or a substituted phenol such as a cresol and an aldehyde such as formaldehyde. The esters of polyhydric phenols are known compounds or may be prepared by known procedures, for example by reaction of the phenols with an acid chloride of a carboxylic acid having a group of formula I, preferably acrylyl chloride or methacrylyl chloride, in the presence of a base. The reaction is usually effected by heating and may be carried out in an inert solvent.

Epoxide resins from which the esters may be derived include those having at least two glycidyl groups attached to an atom or atoms of oxygen, nitrogen or sulphur, and cycloaliphatic epoxide resins in which the epoxide group is part of the ring system. The polyglycidyl compounds may be polyglycidyl esters of aliphatic, cycloaliphatic or aromatic polycarboxylic acids such as adipic, succinic, hexahydrophthalic and phthalic acids, and poly-(N-glycidyl) compounds, for example poly(N-glycidyl) derivatives of aromatic amines such as aniline and bis(4-aminophenyl)methane and hydantoins such as 5,5-dimethylhydantoin. Preferred epoxide resins are polyglycidyl ethers, which may have been advanced, of polyhydric alcohols or phenols, including polyglycidyl ethers of the polyhydric alcohols and polyhydric phenols mentioned above. Preferred polyglycidyl ethers are diglycidyl ethers, which may have been advanced, of dihydric alcohols and phenols, including those of the dihydric alcohols and phenols mentioned above, and polyglycidyl ethers of phenol-aldehyde novolaks. Especially preferred polyglycidyl ethers are diglycidyl ethers, which may have been advanced, of dihydric alcohols having from 2 to 60 carbon atoms, or of bis(4-hydroxyphenyl)methane, 2,2-bis(4-hydroxyphenyl)propane or 2,2-bis(3,5-dibromo-4-hydroxyphenyl)propane, or polyglycidyl ethers of novolaks derived from phenol and formaldehyde. The esters of epoxide resins may be prepared by conventional procedures, for example by reacting the carboxylic acid having a group of formula I, preferably acrylic or methacrylic acid, with the epoxide resin in the presence of a tertiary amine or an onium salt as catalyst.

Compounds having only one group of formula I, that is monoacrylates or monomethacrylates, may be included in the composition either in the absence of substances having 2 or more acrylate or methacrylate groups, or together with such substances. Suitable such monofunctional compounds (B) include hydroxyalkyl acrylates and methacrylates such as 2-hydroxyethyl methacrylate, allyl acrylate and methacrylate, and adducts of monoglycidyl ethers such as phenyl glycidyl ether or iso-octylglycidyl ether with acrylic or methacrylic acid.

When a composition of the invention is to be photopolymerised it should contain (C) a photopolymerisation initiator for acrylic materials which may be any of the known initiators for the photopolymerisation of acrylic materials. Thus (C) may be an aromatic carbonyl compound, preferably a benzoin, a benzoin alkyl ether such as the isopropyl or n-butyl ether, a benzil dialkyl ketal such as benzil dimethyl ketal, an alpha-haloacetophenone such as trichloromethyl p-tert.butylphenyl ketone, an alpha-aminoacetophenone such as dimethylaminomethyl phenyl ketone and morpholinomethyl phenyl ketone, a dialkoxyacetophenone such as diethoxyacetophenone, or a benzophenone such as benzophenone itself and bis(4-dimethylamino)benzophenone; a metallocene, preferably a titanium metallocene such as bis(pi-methylcyclopentadienyl)bis(sigma-pentafluorophenyl) titanium (IV); a Group IVA organometallic compound, preferably a stannane such as trimethyl benzyl stannane, tributyl benzyl stannane or dibutyl benzyl stannane, together with a photoreducible dye, typically methylene blue or rose bengal; a quinone, preferably anthraquinone or camphorquinone, together with an amine having hydrogen attached to an aliphatic alpha carbon atom, preferably a tertiary amine such as bis(4-dimethylamino)benzophenone and triethanolamine; a thioxanthone, preferably an alkyl- or halogen-substituted thioxanthone such as 2-isopropylthioxanthone or 2-chlorothioxanthone; an aliphatic dicarbonyl compound, preferably biacetyl; a ketocoumarin, preferably a coumarin having a carbocyclic or heterocyclic aromatic ketone group in the 3-position, such as 3-benzoyl-7-methoxycoumarin and 3-(4-cyanobenzoyl)-5,7-dipropoxy coumarin; a metal carbonyl, preferably a manganese carbonyl such as dimanganese decacarbonyl; a photo-reducible dye, typically methylene blue or rose bengal, together with a reducing agent, preferably an electron donor such as benzenesulphinic acid or other sulphinic acid or a sodium salt thereof, or an arsine, a phosphine or thiourea; or a mixture of two or more thereof.

When a composition of the invention is to be thermally cured, either directly or after photopolymerisation, it may contain also (D) a thermally activated cationic polymerisation initiator to accelerate the cure. Suitable such initiators include oxy acids, preferably phosphorus-containing acids such as hypophosphorous, phosphonic and phosphinic acids and sulphur-containing acids such as aliphatic and, particularly, aromatic sulphonic acids, and esters of such oxy acids such as diphenyl phosphite; and Lewis acids, such as boron trichloride and boron trifluoride, and complexes thereof with bases such as amines, amides and phosphines. Preferred cationic polymerisation initiators (D) are compounds of formula

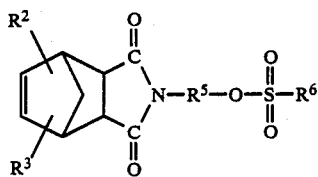

(IX)

where
R² denotes allyl or methallyl,
R³ denotes a hydrogen atom or methyl group,
R⁵ denotes a valency bond, a $C_2$–$C_{20}$ alkylene radical, optionally interrupted in the chain by oxygen atoms, a $C_5$–$C_{20}$ cycloalkylene radical, a $C_6$–$C_{20}$ arylene radical or a group of formula V, and
R⁶ denotes $C_1$–$C_{12}$ alkyl, $C_5$–$C_8$ cycloalkyl, $C_6$–$C_{12}$ aryl or benzyl.

Preferred initiators of formula IX are those where R² denotes allyl, R³ denotes a hydrogen atom, R⁵ denotes a valency bond, a $C_2$ to $C_{10}$ alkylene group, optionally interrupted by oxygen atoms, especially an ethylene, 2,2-dimethylpropylene or —CH₂CH₂OCH₂CH₂— group, a $C_5$ to $C_6$ cycloalkylene group, a $C_6$ to $C_{10}$ arylene group or a group of formula V where X denotes methylene or isopropylidene, and R⁶ denotes $C_1$–$C_6$ alkyl, especially methyl, or $C_6$ to $C_{10}$ aryl, especially phenyl, p-tolyl or 2-naphthyl. An especially preferred compound of formula XVII is allylbicyclo[2.2.1]hept-5-ene-2,3-dicarboxylic acid N-benzenesulphonyloxyimide.

Initiators of formula IX may be prepared by reacting an imide of formula III, where n is 1 and R⁴ denotes —R⁵—OH, with a sulphonyl chloride of formula R⁶—SO₂Cl with cooling and in the presence of an HCl acceptor, preferably a tertiary amine. The reaction is usually carried out in an inert solvent such as toluene.

A thermally activated free radical polymerisation initiator may also be included in a composition of the invention. Suitable free radical initiators are well known and include organic peroxides such as benzoyl peroxide, organic hydroperoxides such as cumene hydroperoxide and azo compounds such as azobis(isobutyronitrile).

In compositions of the invention, the acrylic material may be present in an amount of from 5 to 95%, preferably from 10 to 80%, by weight of the mixture of imide and acrylic materials. When used in image formation the acrylic material is preferably present in an amount from 10 to 50% by weight of this mixture. The photopolymerisation initiator (C) is usually present in an amount of 0.1 to 20%, preferably 1 to 10%, by weight of the mixture of imide and acrylic materials. When a cationic polymerisation initiator (D) is used, it is generally present in an amount of 0.1 to 15%, preferably 0.2 to 5%, by weight of imide material. The compositions of the invention may be liquid or solid, depending on the physical properties of the ingredients and their relative proportions.

Conventional additives such as fillers, plasticisers, pigments, dyes, mould release agents and flame retardants can be included in compositions of the invention. Depending on the use of the composition, it may be dissolved in an inert organic solvent such as toluene, xylene, acetone, methyl ethyl ketone, ethylene glycol monoalkyl and dialkyl ethers containing 1 to 4 carbon atoms in the alkyl groups, N,N-dimethylformamide, N,N-dimethylacetamide, N-methylpyrrolidone, and mixtures of two or more thereof.

The invention also provides a process for the preparation of polymeric material which comprises subjecting a composition of the invention to actinic radiation until it is photopolymerised. The radiation may be exclusively ultraviolet radiation or it may be radiation having wavelengths in both the ultraviolet and visible regions of the spectrum. Radiation having a wavelength of 200 to 600 nm, especially 200 to 400 nm, is preferred. The selection, from commercially available equipment, of a suitable radiation source emitting radiation within this wavelength range is a routine matter for those skilled in the art of photopolymerisation. Suitable sources include medium pressure mercury arc lamps and metal halide lamps. Suitable irradiation times may similarly be determined readily by those familiar with photopolymerisation techniques.

The photopolymerised composition may be further cured by heating. Thus a cured polymeric material may be produced by heating a polymeric material prepared by photopolymerisation of a composition of the invention until it is cured. The temperature at which heat curing is effected and heating times may vary according to the use of the composition. In general, the photopolymerised composition is heated at a temperature of 70° to 300° C., usually for 10 minutes to 6 hours. When used in the production of laminates, for example, the photopolymerised composition is usually heated at 180° to 300° C., preferably 200° to 270° C., normally for 1 to 4 hours. When used in image formation, the photopolymerised composition may, if desired, be heat cured, usually by heating at a temperature of 80° to 120° C., normally for 5 minutes to 1 hour.

The invention also provides a process for the preparation of a cured polymeric material which comprises heating a composition of the invention until it is cured. In such a direct heat-curing process, the composition is usually heated at 70° to 300° C., preferably 180° to 300° C., more preferably 200° to 270° C. It may be advantageous to carry out heat cure initially at a temperature at the lower end of this range, followed by subsequent heating at one or more higher temperatures within the range. When a cured material having maximum physical strength is required, the heat cure may be carried out for durations up to 24 hours. Cure time can be reduced by including an initiator (D) in the composition.

Compositions of the invention can be polymerised and cured to give products having high glass transition temperatures, and thermal stability. They can be used as casting resins, adhesives, laminating resins, coating resins, encapsulating resins and in image formation.

When used as an adhesive, to bond substrates neither of which is transparent to actinic radiation, a composition of the invention may be subjected to actinic radiation until it forms a photopolymerised film which is then placed between, and in contact with, the surfaces to be bonded together, and the assembly is heated to effect cure.

The compositions of the invention are particularly useful in the production of fibre-reinforced resin prepregs and cured composites. Thus the invention provides a prepreg comprising an essentially solid film of a composition of the invention containing a fibrous reinforcing material. When the composition is in solid form, a prepreg may be obtained by impregnating the fibrous reinforcing material with a solution of the composition in an organic solvent such as toluene, xylene, methyl ethyl ketone, ethylene glycol monoalkyl and dialkyl ethers and other solvents used conventionally in the manufacture of prepregs, and then removing the solvent, or by bringing together a film of the composition and the fibrous material under conditions such that the film flows about the fibrous material to form a coherent structure. The prepreg may then be subjected to actinic radiation to photpolymerise the composition.

When the composition of the invention is in liquid form, a preferred method of obtaining a prepreg comprises impregnating a fibrous reinforcing material with the composition in liquid form and irradiating the impregnated material or heating it at 60° to 160° C. until the composition is polymerised to an essentially solid but still heat-curable film. An alternative method of producing a prepreg from the composition in liquid form comprises irradiating, or heating at 60° to 160° C., a layer of the composition in liquid form until it is polymerised to an essentially solid but still heat-curable film and bringing together the film and fibrous reinforcing material under conditions such that the film flows about the fibrous material to form a coherent structure.

A cured composite may be produced by heating, usually under pressure at 180°-300° C., a prepreg of the invention, in which the composition is in solid form, optionally together with other prepregs or fibrous layers, until the composition is cured.

The fibrous reinforcing material may be in the form of woven or nonwoven cloth, unidirectional lengths or chopped strands, especially of glass, carbon, boron, stainless steel, tungsten, alumina, silicon carbide, asbestos, an aromatic polyamide, polyethylene or polypropylene. When a prepreg is produced by bringing together a film and fibrous material, the film may be caused to flow about the fibrous material by the application of heat and/or pressure. Heated platens or pairs of rollers may be used, for example, and in the latter case, when unidirectional fibres are used, a rolling pressure may be applied in the direction of fibre alignment.

The compositions of the invention are also particularly useful in image-forming processes, especially those used in the production of printing plates and printed circuits. Thus the invention also provides a method of forming an image which comprises subjecting a layer of a composition of the invention containing (C) to actinic radiation in a predetermined pattern until the composition is photopolymerised in exposed areas, and removing the composition from unexposed areas. The expression "subjecting . . . to actinic radiation in a predetermined pattern" includes exposure through an image-bearing transparency and exposure to an energy beam such as a laser beam moved as directed by a computer to form an image. The layer of photopolymerisable compositon may be applied from solution in an inert solvent, using conventional techniques, to a substrate such as a metal, a plastics material or a metal-clad plastics laminate. After imagewise exposure in a conventional manner to a source of actinic radiation as hereinbefore described, development of an image is carried out by removing unpolymerised composition from unexposed areas of the layer, usually by dissolution in a solvent such as ethanol, acetone, mixtures thereof and mixtures of either or both with water. As already indicated, the residual photopolymerised composition may be cured by heating, resulting in an image of excellent thermal stability.

The invention is illustrated by the following Examples in which, unless otherwise indicated, parts and percentages are by weight.

Allylbicyclo[2.2.1]hept-5-ene-2,3-dicarboxylic acid N-benzenesulphonyloxyimide, which is used in the Examples, is prepared as follows:

Hydroxylamine hydrochloride (139 g) is dissolved in 200 ml of water; allylbicyclo[2.2.1]hept-5-ene-2,3-dicarboxylic anhydride (408 g) is added to the solution and 50% aqueous sodium hydroxide solution (160 g) is subsequently introduced dropwise with vigorous stirring. The mixture is afterwards refluxed for 1 hour; the water and traces of oily constituents are distilled off, the residue is taken up in toluene, the sodium chloride is filtered off, and the toluene is removed in a rotary evaporator at 150° C. and 2000 Pa. There remain 402.6 g of allylbicyclo[2.2.1]hept-5-ene-2,3-dicarboxylic acid-N-hydroxyimide (91.5% of theory) in the form of a light-brown viscous liquid having a viscosity of 1.28 Pa s at 80° C. (Epprecht viscometer).

| Analysis | calculated | found |
|---|---|---|
| % C | 65.75 | 65.34 |
| % H | 5.98 | 6.02 |
| % N | 6.39 | 6.40 |

The N-hydroxyimide is dissolved in 1 liter of toluene; triethylamine (222.8 g) is added, and stirring is maintained until a homogeneous solution is formed. The solution is cooled to 0° C. and, with vigorous stirring and external cooling, benzene-sulfonyl chloride (324.7 g) is added dropwise in such a manner that the temperature of the reaction mixture remains between 5° and 10° C. The mixture is stirred overnight at room temperature, water is added, the pH value is adjusted to 5 with concentrated hydrochloric acid, and the mixture is subsequently washed twice with water at 75° C. After separation of the aqueous phase, the product is dried over $Na_2SO_4$, filtered, and concentrated in a rotary evaporator at 110° C. and 2000 Pa. The yield is 471 g of a viscous liquid which crystallises on standing (m.p.=97°-99° C.).

| Elementary analysis: | calculated | found |
|---|---|---|
| % C | 60.16 | 60.35 |
| % H | 4.77 | 4.85 |
| % N | 3.90 | 3.90 |
| % S | 8.92 | 8.59 |

IR spectrum (cm$^{-1}$): 575.4, 685.5 and 736.2 aryl; 1195 and 1398 —$SO_2O$—; 1620 cycl. double bond; 1640 allyl double bond; 1742 carbonyl.

EXAMPLE 1

A mixture of N,N'-hexamethylene-bis(allylbicyclo[2.2.1]-hept-5-ene-2,3-dicarboximide) (35 parts) and N-ally-allylbicyclo[2.2.1]hept-5-ene-2,3-dicarboximide (5 parts) is heated at 120° C. until molten. Butane diol-4,1-dimethacrylate (8 parts) is added and the mixture is allowed to cool. To the cooled mixture are added allyl methacrylate (2 parts), benzil dimethyl ketal (1 part) and allylbicyclo[2.2.1]hept-5-ene-2,3-dicarboxylic acid N-benzenesulphonyloxyimide (0.2 part). The resulting composition is coated onto siliconised paper as a layer 20 micrometers thick. The layer is irradiated under a 80 w/cm medium pressure mercury arc lamp at a distance of 20 cm for 30 seconds to give a tack-free film. This film is removed from the siliconised paper and heated at 250° C. for 2 hours to produce a cured, hard film having a glass transition temperature of 285°–290° C. as determined by thermomechanical analysis (penetration).

EXAMPLE 2

A mixture of N,N'-hexamethylene-bis(allylbicyclo[2.2.1]hept-5-ene-2,3-dicarboximide) (70 parts) and N-allyl-allylbicyclo[2.2.1]-hept-5-ene-2,3-dicarboximide (10 parts) is heated at 120° C. until molten. 1,1,1-trimethylolpropane trismethacrylate (16 parts) is added and the mixture is allowed to cool. To the cooled mixture are added allyl methacrylate (4 parts), benzil dimethyl ketal (2 parts) and allylbicyclo[2.2.1]hept-5-ene-2,3-dicarboxylic acid N-benzenesulphonyloxyimide (0.4 part). The resulting composition is used to impregnate a woven carbon fibre mat. The impregnated mat, having a resin content of 65.1%, is irradiated on both sides with a 80 w/cm medium pressure mercury arc lamp at a distance of 10 cm. for 10 seconds to give a solid, tacky prepreag. A 12-ply laminate is made by heating twelve 10 cm square pieces of the prepreg at 250° C. for 2 hours under a pressure of 1.4 MN/m$^2$. The resulting laminate has a resin content of 58.2% and an interlaminar shear strength of 22.3 MN/m$^2$ at room temperature.

EXAMPLE 3

A mixture of bis[4-(allylbicyclo[2.2.1]hept-5-ene-2,3-dicarboximidophenyl)]methane (30 parts), N,N'-hexamethylene-bis(allylbicyclo[2.2.1]hept-5-ene-2,3-dicarboximide) (30 parts) and N-allylallylbicyclo[2.2.1]hept-5-ene-2,3-dicarboximide (10 parts) is heated at 120° C. until molten. 1,1,1-trimethylolpropane trismethacrylate (25 parts) is added and the mixture is allowed to cool. To the cooled mixture are added allyl methacrylate (5 parts), benzil dimethyl ketal (2 parts) and allylbicyclo[2.2.1]-hept-5-ene-2,3-dicarboxylic acid N-benzenesulphonyloxyimide (0.4 part). The resulting composition is used to impregnate a woven carbon fibre mat. The impregnated mat, having a resin content of 63.1%, is irradiated as described in Example 2 to give a tack-free prepreg. A 12-ply laminate is made by heating twelve 10 cm square pieces of the prepreg at 250° C. for 2 hours under a pressure of 1.4 MN/m$^2$. The resulting laminate has a resin content of 58.0%, and interlaminar shear strengths of 21.4 MN/m$^2$ at room temperature and 13.5 MN/m$^2$ at 135° C.

EXAMPLE 4

A mixture of bis[4-(allylbicyclo[2.2.1]hept-5-ene-2,3-dicarboximidophenyl)]methane (1 part), tris(2-acryloyloxyethyl)isocyanurate (0.2 part) and 1-hydroxycyclohexylphenylketone (0.05 part) are dissolved in dimethylformamide (2 parts). A layer of the composition 24 micrometers thick is coated onto a copper-clad laminate and dried at 90° C. for five minutes to produce a tack-free film. The film is irradiated through a negative using a 5000 w metal halide lamp at a distance of 80 cm for 5 minutes. Development in ethanol results in a negative image.

EXAMPLE 5

Example 4 is repeated, using bis(4-dimethylamino)-benzophenone (0.05 part) instead of 1-hydroxycyclohexylphenylketone. On development in ethanol, a negative image is formed.

EXAMPLE 6

Example 4 is repeated, using benzildimethylketal (0.05 part) instead of 1-hydroxycyclohexylphenylketone. On development in ethanol, a negative image is formed.

EXAMPLE 7

Example 4 is repeated, using 2-isopropylthioxanthone (0.05 part) instead of 1-hydroxycyclohexylphenylketone. On development in ethanol, a negative image is formed.

EXAMPLE 8

A mixture of bis[4-(allylbicyclo[2.2.1]hept-5-ene-2,3-dicarboximidophenyl)]methane (1 part), tris(2-acryloyloxyethyl)isocyanurate (0.2 part) and bis(pi-methylcyclopentadienyl) bis(sigma-pentafluorophenyl)-titanium (IV) (0.05 part) are dissolved in a mixture of N-methylpyrrolidone (1 part) and acetone (0.45 part). A layer of the composition 24 micrometers thick is coated onto a copper-clad laminate and dried at 90° C. for 5 minutes to product a tack-free film. This film is irradiated through a negative using a 5000 w metal halide lamp at a distance of 80 cm for 2 minutes. The irradiated film is then heated at 90° C. for 15 minutes and developed in a mixture of 90% by volume of ethanol and 10% by volume of acetone. A clear negative image is formed. Thermogravimetric analysis of the image, i.e. the cured material, in nitrogen shows a 13.9% weight loss on rising from room temperature to 400° C. at the rate of 10° C. per minute, and 17.4% weight loss on holding at 400° C. for 1 hour, giving a total weight loss of 31.3%.

EXAMPLE 9

A mixture of bis[4-(allylbicyclo[2.2.1]hept-5-ene-2,3-dicarboximidophenyl)]methane (1 part), dipentaerythritol monohydroxypentacrylate (0.2 part), benzil dimethyl ketal (0.05 part) and a fluorocarbon surfactant (one drop of a 1% solution in 2-butoxyethanol) are dissolved in N-methylpyrrolidone (1 part). A layer of the composition 24 micrometers thick is coated onto an aluminium sheet and dried at 90° C. for five minutes to produce a tack-free film. This film is irradiated through a negative using a 5000 w metal halide lamp at a distance of 80 cm for 5 minutes. The irradiated film is heated at 90° C. for 15 minutes and development in a mixture of 90% by volume of ethanol and 10% by volume of acetone. A clear negative image is formed.

EXAMPLE 10

A mixture of bis[4-(allylbicyclo[2.2.1]hept-5-ene-2,3-dicarboximidophenyl)]methane (1 part), pentaerythritol tetraacrylate (0.2 part) and 1-hydroxycyclohexylphenylketone (0.05 part) are dissolved in N-methylpyrrolidone (2 parts). A layer of the composition 24 micrometers thick is coated onto tinplate and dried at 90° C. for five minutes to produce a tack-free film. This film is irradiated through a negative using a 5000 w metal halide lamp at a distance of 80 cm for 5 minutes. The irradiated film is then heated at 90° C. for 15 minutes and developed in a mixture containing, by volume, 90% of ethanol and 10% of acetone. A clear negative image is produced.

EXAMPLE 11

A mixture of bis[4-allylbicyclo[2.2.1]hept-5-ene-2,3-dicarboximidophenyl)]methane (1 part), butane diol-1,4-dimethacrylate (0.15 part) and 2-isopropylthioxanthone (0.1 part) is dissolved in N-methylpyrrolidone. A layer of the composition 24 micrometers thick is coated onto a copper-clad laminate and dried at 90° C. for five minutes to produce a tack-film. The film is irradiated through a negative using a 5000 w metal halide lamp at a distance of 80 cm for 5 minutes. The irradiated film is then developed in a mixture containing, by volume, 90% of ethanol and 10% of water to give a clear negative image.

EXAMPLE 12

A mixture of bis[4-(allylbicyclo[2.2.1]hept-5-ene-2,3-dicarboximidophenyl)]methane (1 part), tris(2-acryloyloxyethyl) isocyanurate (0.2 part), allylbicyclo[2.2.1]hept-5-ene-2,3-dicarboxylic acid N-benzenesulphonyloxyimide (0.01 part) and bis(pi-methylcyclopentadienyl)bis(sigma-pentafluorophenyl)titanium (IV) (0.05 part) is dissolved in a mixture of N-methylpyrrolidone (2 parts) and acetone (0.45 part). A layer of the composition 24 micrometers thick is coated onto a copper-clad laminate and dried at 90° C. for five minutes to produce a tack-free film. The film is irradiated through a negative using a 5000 w metal halide lamp at a distance of 80 cm for 2 minutes. The irradiated film is heated at 90° C. for 15 minutes and developed in a mixture containing, by volume, 90% of ethanol and 10% of acetone to give a clear negative image. Thermogravimetric analysis of this image in nitrogen to determine stability of the cured material gives the following results:

| | weight loss (%) |
|---|---|
| Room temperature to 400° C. (10° C. min$^{-1}$) | 8.7 |
| Hold at 400° C. for one hour | 8.7 |
| TOTAL | 17.4 |

EXAMPLES 13–24

Bis[4-(allylbicyclo[2.2.1]hept-5-ene-2,3-dicarboxyimidophenyl)]methane (100 parts) is melted at 150° C. and 4tert.butyl-1,2-dihydroxybenzene (0.05 part) is added followed by an acrylic ester to give a resinous syrup, whose viscosity is measured at 25° C., 40° C. or 80° C. The syrup is poured into 150×150×4 mm$^3$ steel moulds having their surface treated with a silicone release agent. The moulds are degassed and cure is then effected by heating for 2 hours at 200° C., 2 hours at 225° C. and 12 hours at 250° C. to give hard plates of excellent quality. These plates are sawn to give test bars for physical property measurements.

The nature and amount of the acrylic ester and any additional ingredient used in the different Examples, together with the results of the measurements, are shown in Table 1, in which phr denotes the amount of acrylic ester per 100 parts by weight of the allylnadicimide, η denotes viscosity in Pa s, Tv denotes the temperature at which the viscosity is measured, Tg denotes glass transition temperature, HDT denotes heat deflection temperature, measured in accordance with ISO 75, FS denotes flexural strength, measured in accordance with ISO 178, El denotes elongation, measured in accordance with ISO 178, IS denotes impact strength, measured in accordance with ISO 179, and $WA_r$ and $WA_{100}$ denote water absorption after immersion in water at room temperature for 4 days and at 100° C. for 1 hour respectively, expressed as a percentage by weight of the test sample.

TABLE 1

| Ex. | Acrylic Ester and additional ingredient | phr parts | η Pa s | Tv °C. | Tg °C. | HDT °C. | FS N/mm$^2$ | E % | IS KJ/m$^2$ | $WA_r$ % | $WA_{100}$ % |
|---|---|---|---|---|---|---|---|---|---|---|---|
| 13 | TCD-Acrylate[4] | 50 | 5,9 | 25 | 183 | — | 71,5 | 2,1 | 3,5 | — | — |
| 14 | Butanediol-1,4-diacrylate | 50 | 5,9 | 25 | 169 | 185 | 90,0 | 6,9 | 13,0 | 1,9 | 1,4 |
| 15 | Neopentylene glycol diacrylate | 50 | 1,43 | 40 | — | >250 | 103,4 | 3,9 | 7,46 | 1,0 | 0,65 |
| 16 | Hexanediol-1,6-diacrylate | 50 | 0,38 | 25 | — | 234 | 90,5 | 3,9 | 9,37 | 1,25 | 0,9 |
| 17[1] | Hexanediol-1,6-diacrylate Polymerisation Catalyst[2] | 50 1 | — | — | 270 | 252 | 75,7 | 3,6 | 6,29 | 1,45 | 0,6 |
| 18 | Hexanediol-1,6-dimethacrylate | 50 | 1,27 | 25 | 301 | >250 | 74,3 | 3,4 | 6,43 | 0.97 | 0,55 |
| 19 | 2,2'-Di(acryloyloxyethoxy)bisphenol A | 40 | 0,69 | 80 | — | >250 | 123,3 | 5,2 | 21,08 | 0,40 | 0,43 |
| 20 | 2,2'-Di(acryloyloxyethoxy)bisphenol A | 50 | 1,35 | 80 | 254 | 149 | 136,2 | 6,0 | 15,1 | 0,46 | 0,38 |
| 21 | 2,2'-Di(methacryloyloxyethoxy)bisphenol A | 50 | 0,77 | 80 | 301 | >250 | 89,1 | 3,5 | 8,64 | 0,84 | 0,52 |
| 22 | Tripropylene glycol diacrylate | 50 | 0,17 | 80 | 172 | 139 | 104 | 6,8 | 8,17 | 0,98 | 0,81 |
| 23 | Glycerol tris(propoxyacrylate) | 50 | 0,68 | 80 | — | 234 | 90.6 | 3,9 | 9,37 | 1,25 | 0,89 |
| 24[3] | Glycerol tris(propoxyacrylate) Polymerisation | 45 1 | — | — | 293 | 239 | 93,7 | 4,7 | 7,76 | | |

TABLE 1-continued

| Ex. | Acrylic Ester and additional ingredient | phr parts | η Pa s | Tv °C. | Tg °C. | HDT °C. | FS N/mm² | E % | IS KJ/m² | WA_r % | WA₁₀₀ % |
|---|---|---|---|---|---|---|---|---|---|---|---|
| | Catalyst² | | | | | | | | | | |

[1] In Example 17, curing is effected by heating for 2 hours at 250° C.
[2] Polymerisation Catalyst denotes allylbicyclo[2.2.1]hept-5-ene-2,3-dicarboxylic acid N-benzenesulphonyloxyimide.
[3] In Example 24, the tert.butyldihydroxybenzene is replaced by the same amount of triethylene glycol bis 3-(3-tert.butyl-4-hydroxy-5-methylpehnyl)propionate and curing is effected by heating at 250° C. for 2 hours.
[4] TCD-acrylate denotes

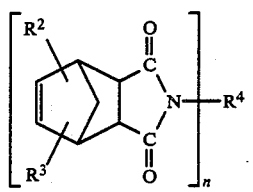

What is claimed is:

1. A polymerizable composition comprising a mixture of
(A) a substance having at least one allyl- or methallyl-substituted bicyclo[2.2.1]-hept-5-ene-2,3-dicarboxylic acid imide residue and having formula III

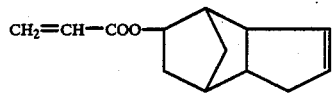

where
n denotes 1, 2 or 3,
$R^2$ denotes allyl or methallyl,
$R^3$ denotes a hydrogen atom or methyl group, and
when n is 1, $R^4$ denotes a hydrogen atom, a hydroxyl group, or an organic group selected from $C_1$-$C_{40}$-alkyl, $C_1$-$C_{40}$-alkyl interrupted in the chain by oxygen atoms, $C_3$-$C_6$-alkenyl, $C_5$-$C_{20}$-cycloalkyl, $C_6$-$C_{20}$-aryl or benzyl, any of said organic groups being substituted or unsubstituted by a hydroxyl group, or a group of formula IV $$-Ar^1-X-Ar^2-OH \quad \text{IV}$$

where $Ar^1$ and $Ar^2$ each denote a phenylene group and X denotes methylene, isopropylidene, —CO—, —O—, —S— —SO₂—, or
when n is 2, $R^4$ denotes $C_2$-$C_{20}$-alkylene, $C_2$-$C_{20}$-alkylene interrupted in the chain by oxygen atoms or secondary amino groups, $C_6$-$C_{20}$-arylene or a group of formula V $$-Ar^1-X-Ar^2- \quad \text{V}$$

where $Ar^1$, $Ar^2$ and X are as defined in formula IV, or
when n is 3, $R^4$ denotes a group of formula VI

Y denotes >P=O or >P— and R denotes an alkylene group of 2 to 40 carbon atoms, $C_2$-$C_{40}$-alkylene in the chain by oxygen atoms, a m-or p-phenylene group, or a m- or p-phenyleneoxy group in which the oxygen atom is bonded to the group Y, or
Y denote >CH— and R denotes a m- or p-phenylene group, or
Y denotes $CH_3CH_2C(CH_2)_3$ or —$CH_2CHCH_2$— and R denotes an oxyalkylene group of 2 or 3 carbon atoms, a polyoxyethylene or polyoxypropylene group of 4 to 40 carbon atoms, or a m- or p-phenyleneoxy group in which the oxygen atom it attached to the group Y, or
Y denotes N- and R denotes an alkylene group of 2 to 10 carbon atoms, or a m- or p-phenylene group, and
(B) an acrylic material having at least one polymerizable residue of formula I $$CH_2=C(R^1)COO— \quad \text{I}$$

where $R^1$ denotes a hydrogen atom or a methyl group.

2. A composition according to claim 1, in which $R^2$ denotes allyl and $R^3$ denotes a hydrogen atom.

3. A composition according to claim 1, in which
n is 1 and $R^4$ denotes a hydrogen atom, a hydroxyl group, $C_1$-$C_8$ alkyl, allyl, cyclohexyl, phenyl or benzyl, $C_2$-$C_8$ alkyl substituted by one or two hydroxyl groups and interrupted or uninterrupted in the chain by 1 to 3 oxygen atoms, hydroxycyclohexyl, hydroxyphenyl, or a group of formula IV where X denotes methylene, isopropylidene, —O—, or —SO₂—, or
n is 2 and $R^4$ denotes $C_2$-$C_{12}$ straight chain alkylene, m- or p-phenylene or a group of formula V where X denotes methylene, —O— or —SO₂—, or
n is 3 and $R^4$ denotes a group of formula VI where
Y denotes >P=O or >P— and R denotes an alkylene group of 2 to 4 carbon atoms, a m- or p-phenylene group or a m-or p-phenyleneoxy group, or
Y denotes >CH— and R denotes a p-phenylene group, or
Y denotes $CH_3CH_2C(CH_2)_3$ and R denotes a group —[$CH_2CH(CH_3)O$]—$_r$ where r is 1, 2 or 3, or
Y denotes —$CH_2CHCH_2$— and R denotes a group —($CH_2CH_2O$)—$_r$ where r is 1, 2 or 3, or a m- or p-phenyleneoxy group, or
Y denotes >N— and R denotes an ethylene, trimethylene, or m- or p-phenylene group.

4. A composition according to claim 3, in which $R^2$ denotes allyl, $R^3$ denotes a hydrogen atom and
n is 1 and $R^4$ denotes a hydroxyl group, allyl, 2-hydroxyethyl, or p-hydroxyphenyl, or
n is 2 and $R^4$ denotes —($CH_2$)₆—,

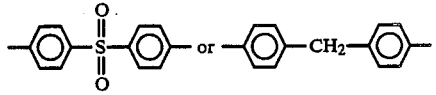

or n is 3 and $R^4$ denotes

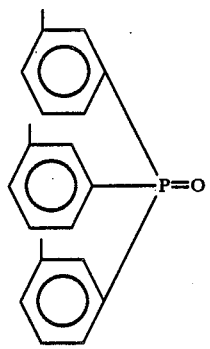

5. A composition according to claim 1, in which the acrylic material is an ester of a carboxylic acid containing a group of formula I and a polyhydric alcohol or phenol or an epoxide resin.

6. A composition according to claim 5, in which the acrylic material is a polyacrylate or polymethacrylate ester of a polyhydric alcohol having from 2 to 10 alcoholic hydroxyl groups or of a polyglycidyl ether of a polyhydric alcohol or phenol.

7. A composition according to claim 1, which also contains (C) a photopolymerization initiator for acrylic materials.

8. A composition according to claim 1, which also contains (D) a thermally activated cationic polymerization initiator.

9. A composition according to claim 8, in which (D) is an imide of formula

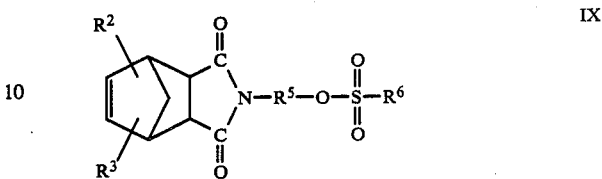

IX where
$R^2$ denotes allyl or methallyl,
$R^3$ denotes a hydrogen atom or a methyl group,
$R^5$ denotes a valency bond, a $C_2$–$C_{20}$ alkylene radical interrupted or uninterrupted in the chain by oxygen atoms, a $C_5$–$C_{20}$ cycloalkylene radical, a $C_6$–$C_{20}$ arylene radical or a group of formula V $$-Ar^1-X-Ar^2-$$  V where $Ar^1$ and $Ar^2$ each denote a phenylene group and X denotes methylene, isopropylidene, —CO—, —O—, —S—, or —SO$_2$—, and
$R^6$ denotes $C_1$–$C_{12}$ alkyl, $C_5$–$C_8$ cycloalkyl, $C_6$–$C_{12}$ aryl or benzyl.

10. A composition according to claim 1, in which (B) is present in an amount 10 to 80% by weight of the mixture of (A) and (B).

11. A composition according to claim 1 photopolymerized by exposure to actinic radiation.

12. A compostion according to claim 1 cured by heating.

* * * * *